US010093603B2

(12) United States Patent
Eom et al.

(10) Patent No.: US 10,093,603 B2
(45) Date of Patent: Oct. 9, 2018

(54) APPARATUS FOR PREPARING GLYCOL AND METHOD OF PREPARING THE SAME

(71) Applicant: LG CHEM, LTD., Seoul (KR)

(72) Inventors: Sung Shik Eom, Daejeon (KR); Da Won Jung, Daejeon (KR); Tae Yun Kim, Daejeon (KR); Jung Uk Choi, Daejeon (KR); Dong Hyun Ko, Daejeon (KR); Mi Young Kim, Daejeon (KR); Min Ji Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 15/538,922

(22) PCT Filed: Aug. 25, 2016

(86) PCT No.: PCT/KR2016/009449
§ 371 (c)(1),
(2) Date: Jun. 22, 2017

(87) PCT Pub. No.: WO2017/043785
PCT Pub. Date: Mar. 16, 2017

(65) Prior Publication Data
US 2017/0349512 A1    Dec. 7, 2017

(30) Foreign Application Priority Data

Sep. 7, 2015  (KR) .................. 10-2015-0126495

(51) Int. Cl.
| | | |
|---|---|---|
| *C07C 29/141* | (2006.01) | |
| *C07C 29/80* | (2006.01) | |
| *B01D 3/10* | (2006.01) | |
| *B01D 3/14* | (2006.01) | |
| *B01J 8/02* | (2006.01) | |
| *B01J 19/24* | (2006.01) | |
| *C07C 29/84* | (2006.01) | |
| *C07C 45/75* | (2006.01) | |
| *C07C 45/80* | (2006.01) | |
| *C07C 45/82* | (2006.01) | |

(52) U.S. Cl.
CPC .............. *C07C 29/141* (2013.01); *B01D 3/10* (2013.01); *B01D 3/141* (2013.01); *B01D 3/143* (2013.01); *B01J 8/02* (2013.01); *B01J 19/245* (2013.01); *C07C 29/80* (2013.01); *C07C 29/84* (2013.01); *C07C 45/75* (2013.01); *C07C 45/80* (2013.01); *C07C 45/82* (2013.01); *B01J 2208/027* (2013.01); *B01J 2219/24* (2013.01)

(58) Field of Classification Search
CPC ......... C07C 29/14; C07C 29/80; C07C 29/82; C07C 31/20; C07C 29/141; C07C 29/84; C07C 45/75; C07C 45/80; C07C 45/82; B01D 3/10; B01D 3/141; B01D 3/143; B01J 19/245; B01J 8/02; B01J 2208/027; B01J 2219/24

See application file for complete search history.

(56) References Cited

U.S. PATENT DOCUMENTS

| | | | |
|---|---|---|---|
| 2,471,134 A | * | 5/1949 | Wright .................... B01D 3/14 196/100 |
| 6,201,159 B1 | * | 3/2001 | Choi .................... C07C 29/141 568/853 |
| 6,201,160 B1 | | 3/2001 | Brudermuller et al. |
| 6,255,541 B1 | * | 7/2001 | Paatero ................ C07C 29/141 568/852 |
| 2015/0239809 A1 | * | 8/2015 | Eisenacher ............ C07C 45/75 568/853 |

FOREIGN PATENT DOCUMENTS

| | | |
|---|---|---|
| KR | 10-1998-0028461 A | 7/1998 |
| KR | 10-0676304 B1 | 1/2007 |
| KR | 10-2012-0076196 A | 7/2012 |
| KR | 10-2014-0126876 A | 11/2014 |
| KR | 10-2015-0076176 A | 7/2015 |
| WO | 2014-120481 A1 | 8/2014 |

* cited by examiner

*Primary Examiner* — Pancham Bakshi
*Assistant Examiner* — Mark R Luderer
(74) *Attorney, Agent, or Firm* — Dentons US LLP

(57) ABSTRACT

The present disclosure relates to an apparatus for generating glycol and a method thereof. More particularly, the present disclosure relates to an apparatus for generating glycol including (a) an aldol reactor; (b) an extractor for extracting an aldol product, unsaturated aldehyde, using an organic solvent that is not mixed with water; (c) a distillation column for removing a raw material from a solution extract that is discharged from the extractor; (d) a hydrogenation reactor for hydrogenating a solution extract that is discharged from the distillation column; and (e) a divided-wall distillation column for isolating glycol from a hydrogenated solution product that is discharged from the hydrogenation reactor, wherein the hydrogenation reactor is a fixed-bed catalytic reactor that is filled with a copper-based catalyst, and a method of preparing the same.
In accordance with the present disclosure, an economical apparatus for preparing glycol which reduces loss of a raw material and provides a high glycol yield while inhibiting generation of by-products, and a method of preparing the same are provided.

14 Claims, 1 Drawing Sheet

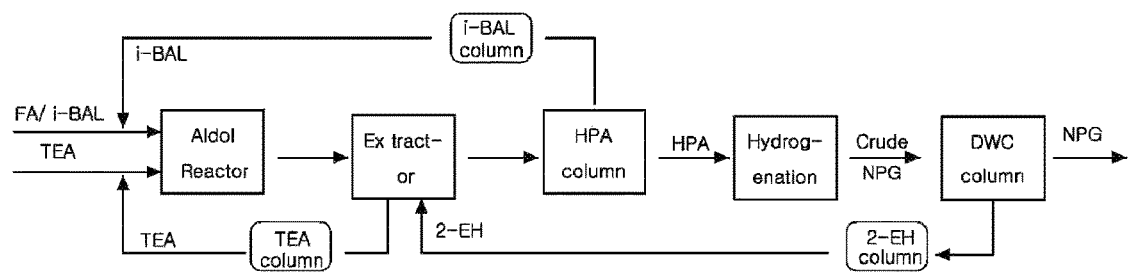

APPARATUS FOR PREPARING GLYCOL AND METHOD OF PREPARING THE SAME

CROSS-REFERENCE TO RELATED APPLICATION(S)

This application is a National Stage Entry of International Application No. PCT/KR2016/009449, filed Aug. 25, 2016, and claims the benefit of and priority to Korean Application No. 10-2015-0126495, filed on Sep. 7, 2015, all of which are hereby incorporated by reference in their entirety for all purposes as if fully set forth herein.

TECHNICAL FIELD

The present disclosure relates to an apparatus for preparing glycol and a method of preparing the same. More particularly, the present disclosure relates to an economical apparatus for preparing glycol which reduces loss of a raw material and provides a high neopentyl glycol yield while inhibiting generation of by-products, and a method of preparing the same.

BACKGROUND ART

A glycol is an organic compound with two hydroxyl groups attached to different carbon atoms thereof. Particularly, neopentyl glycol (NPG), which is a white crystalline material with a melting point of 129.13° C., is an important intermediate of various synthetic resins. In addition, NPG is widely used industrially as a raw material of various plastic powder coatings, synthetic lubricants, plasticizers, surfactants, textile finishing agents, and the like.

Such NPG is generally prepared by aldol-condensing isobutyraldehyde with formaldehyde to produce hydroxypivaldehyde (HPA), and then reacting HPA with hydrogen in the presence of a catalyst as in Formula 1 below:

[Formula 1]

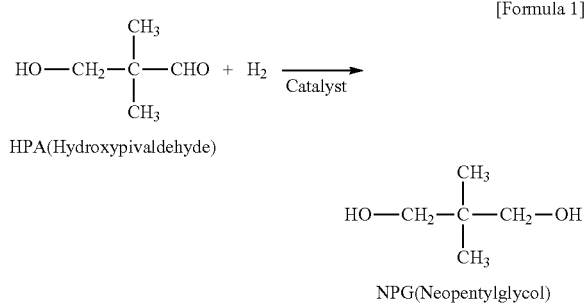

In aldol condensation between isobutyraldehyde and formaldehyde, an alkali metal compound, such as an alkaline hydroxide or an alkaline carbonate, has been used as a catalyst. However, when such alkali metal compounds are used, a large amount of organic acid salts is generated and there have been problems in separating and treating by-products thereof.

In U.S. Pat. No. 3,808,280, a tertiary amine was used as a catalyst useful for aldol condensation reaction. Although the yield of HPA increases when aldol condensation is performed using a tertiary amine, a tertiary amine salt, which is generated due to reaction of the tertiary amine with organic acid in a reaction mixture, inactivates a hydrogenation catalyst such as Raney nickel. In addition, the tertiary amine salt decomposes HPA at high temperature, which is a direct cause of NPG yield decrease and catalyst poisoning.

As a main by-product of aldol condensation reaction, isobutyl aldoxane, NPG-isobutyrate, or the like is generated. Such isobutyl aldoxane, NPG-isobutyrate, or the like is converted into a by-product, such as isobutanol or trimethylpentanediol (2,2,4-trimethyl-1,3-pentanediol; TMPD), by hydrogenation. Since these by-products have a boiling point similar to that of NPG, it is very difficult to isolate the same by distillation.

In U.S. Pat. No. 4,885,515, a triethylamine catalyst was not isolated from a product of aldol condensation reaction, and hydrogenation was directly performed using a copper chromite catalyst containing manganese. However, such hydrogenation should be performed under conditions of high temperature and high pressure, thereby requiring expensive equipment. In addition, since a catalyst is inactivated during hydrogenation, the catalyst should be replaced. These are disadvantages preventing commercialization of the method.

In U.S. Pat. No. 4,851,592, hydrogenation was performed in a slurry state using Raney nickel by means of a gas-sparging reactor. However, in this case, since crude HPA is directly fed into a hydrogenation reactor when hydrogenation is performed, catalyst poisoning due to the organic acid salt of a tertiary amine or unreacted substances, which are contained in a reactant, is serious. Accordingly, there are problems in performing the hydrogenation for a long time.

In addition, since an aqueous formaldehyde solution containing 8 to 15% by weight of methanol is used as a reactant in conventional aldol condensation reaction, methanol is discharged along with wastewater after the reaction. Accordingly, a separate process of separating and distilling methanol is required. Therefore, the process is complicated and equipment costs are high.

Crude NPG, which is a hydrogenation product, includes TMPD, hydroxypivalic acid NPG ester (HPNE), and the like. Since TMPD and HPNE have boiling points very similar to that of NPG, it is impossible to isolate the TMPD and HPNE by simple distillation. In addition, since, when a reaction mixture is distilled, HPNE is unstable and the yield of NPG is decreased, sodium hydroxide is added to be converted into NPG by saponification in the industry. However, since HPA or sodium salts of other organic acids, which have been generated by saponification, promote decomposition reaction of NPG at a high temperature of 140° C. or more, a distillation process is restricted. In addition, it is impossible to remove TMPD that is not converted into a nonvolatile sodium salt during saponification.

Accordingly, various methods of purifying NPG from crude NPG have been suggested. For example, a method of extracting using a solvent, a vacuum distillation method, a crystallization method, and the like have been suggested. However, these methods are not economical and commercialization thereof is thus difficult.

U.S. Pat. No. 2,895,996 proposed a method of sublimating crude NPG by saponification to obtain high-purity NPG. Here, a distillation temperature is limited to 70° C. to 140° C. to prevent decomposition of NPG by sodium salt, whereby the temperature of an upper part of a sublimation apparatus is low. Accordingly, the method is uneconomical.

U.S. Pat. No. 4,935,555 proposed a method of distilling NPG by means of a thin-film vacuum distillation apparatus. However, the method is uneconomical due to high equipment costs. In addition, the recovery rate of NPG is decreased due to side reactants and distillation residues and it is impossible to isolate TMPD that is not converted into a salt during saponification, whereby purity is decreased.

Therefore, attempts to produce NPG in high yield and using economical manner are ongoing.

DISCLOSURE

Technical Problem

Therefore, the present invention has been made in view of the above problems, and it is one object of the present invention to provide an economical apparatus for preparing glycol which reduces loss of a raw material and provides a high glycol yield while inhibiting generation of by-products, and a method of preparing the same.

The above and other objects can be accomplished by the present disclosure described below.

Technical Solution

In accordance with an aspect of the present invention, the above and other objects can be accomplished by the provision of an apparatus for generating glycol including (a) an aldol reactor; (b) an extractor for extracting an aldol product, unsaturated aldehyde, using an organic solvent that is not mixed with water; (c) a distillation column for removing a raw material from a solution extract that is discharged from the extractor; (d) a hydrogenation reactor for hydrogenating a solution extract that is discharged from the distillation column; and (e) a divided-wall distillation column for isolating glycol from a hydrogenated solution product that is discharged from the hydrogenation reactor, wherein the hydrogenation reactor is a fixed-bed catalytic reactor that is filled with a copper-based catalyst.

The aldol reactor (a) may be, for example, a jacketed reactor.

The aldol product of the extractor (b) may be, for example, hydroxypivaldehyde, and the glycol of the divided-wall distillation column (e) may be, for example, neopentyl glycol.

The extractor may include, for example, an aldol product inlet, an extractant inlet, an organic layer outlet, and a water layer outlet.

By vacuum distillation, a raw material may be discharged, for example, from an upper part of the distillation column (c) and a solution extract including unsaturated aldehyde may be, for example, discharged from a lower part of the distillation column (c)

The apparatus may further include, for example, a reaction tank in which ion-exchange reaction occurs by adding an inorganic base to a water layer, an aqueous solution, discharged from the extractor (b); and a catalyst recovery column for recovering a catalyst for aldol reaction by distilling a basic aqueous solution discharged from the reaction tank.

The apparatus may further include, for example, a water supply pipe for supplying water to a solution extract discharged from the distillation column (c).

The apparatus may further include, for example, an aldehyde recovery column for recovering a start material, an aldehyde compound, from a raw material discharged from the distillation column (c).

The copper-based catalyst may be, for example, a CuO/BaO catalyst, particularly a CuO/BaO/SiO catalyst.

An organic solvent and water may be separated and discharged, for example, from an upper part of the divided-wall distillation column, a material having a high boiling point may be separated and discharged, for example, from a lower part of the divided-wall distillation column, and glycol may be discharged, for example, from an intermediate part of the divided-wall distillation column.

In accordance with another aspect of the present invention, there is provided a method of preparing glycol by means of the apparatus.

The method may further include, for example, a step of adding isobutyraldehyde, an aqueous formaldehyde solution, and an amine compound to an aldol reactor (a) and performing aldol condensation reaction at 70 to 95° C.

In the method, an organic solvent supplied to an extractor (b) may be, for example, a polar organic solvent.

In the method, a solution extract fed into a hydrogenation reactor (d) may include, for example, 1 to 20% by weight of water based on 100% by weight of the solution extract.

Advantageous Effects

As apparent from the above description, the present invention provides an economical apparatus for preparing glycol which reduces loss of a raw material and provides a high glycol yield while inhibiting generation of by-products, and a method of preparing the same.

DESCRIPTION OF DRAWINGS

The drawing is a flowchart schematically illustrating a process of continuously preparing neopentyl glycol according to the present disclosure and an apparatus therefor.

BEST MODE

Hereinafter, an apparatus for preparing glycol and a method thereof according to the present disclosure are described in detail.

An apparatus for generating glycol of the present disclosure includes (a) an aldol reactor; (b) an extractor for extracting an aldol product, unsaturated aldehyde, using an organic solvent that is not mixed with water; (c) a distillation column for removing a raw material from a solution extract that is discharged from the extractor; (d) a hydrogenation reactor for hydrogenating a solution extract that is discharged from the distillation column; and (e) a divided-wall distillation column for isolating glycol from a hydrogenated solution product that is discharged from the hydrogenation reactor, wherein the hydrogenation reactor is a fixed-bed catalytic reactor that is filled with a copper-based catalyst.

The aldol reactor (a) may be, for example, a jacketed reactor or a CSTR reactor. The aldol reactor (a) is preferably a series CSTR reactor, more preferably a series CSTR reactor in which two to five reactors are connected. In this case, it is easy to control a ratio of a raw material supplied to each reactor and the temperature of each reactor may be differently controlled depending upon reaction progress degree. Accordingly, the yield of aldol condensation reaction is superior.

The series CSTR reactor refers to a reactor in which a plurality of CSTRs is connected in series.

The aldol product of the extractor (b) may be, for example, hydroxypivaldehyde (HPA), and the glycol of the divided-wall distillation column (e) may be neopentyl glycol (NPG).

The extractor may include, for example, an aldol product inlet, an extractant inlet, an organic layer outlet, and a water layer outlet. In this case, triethylamine salt, formaldehyde, and the like, which cause catalyst poisoning, are removed, whereby hydrogenation of unsaturated aldehyde may be stably, continuously performed for a long time.

The extractor may be a CSTR reactor-type extractor. However, when the CSTR reactor-type extractor is used, the number of reactors should be increased or a total volume of the extractor increases. Accordingly, it is advantageous to use a multi-stage extractor in terms of extraction efficiency and economic feasibility.

The multi-stage extractor may be, for example, a 10 to 50-stage extractor or 20 to 40-stage extractor. Within this range, superior extraction efficiency is provided.

The organic solvent (extractant) is suitably used, for example, in an amount of 0.3 to 4 times a total weight of unsaturated aldehyde.

In addition, when water is added, along with the organic solvent, in an amount of 1 to 2 times a total weight of unsaturated aldehyde, organic acid, an organic acid salt, and the like, which are water-soluble side reactants, may be more efficiently removed. Further, since unsaturated aldehyde may remain in a water layer when water is added to extract unsaturated aldehyde, the water layer is discharged to a lower part of a column and then isobutyraldehyde (i-BAL) is fed in an amount of 0.3 to 1.5 times total weight of the water layer, as needed, to extract and recover unsaturated aldehyde.

In the extractor, an organic layer, a solution extract, including unsaturated aldehyde and an organic solvent is separated from a water layer, raffinate, including water, a salt, and an acid.

The raffinate, as a water layer, is separated from the solution extract, as an organic layer, and is discharged to a lower part of the extractor. Subsequently, the catalyst for aldol reaction may be recovered by adding an strong inorganic base, such as NaOH. The recovered catalyst may be reused and thus is very economical.

For example, when an amine compound is used as a catalyst for aldol reaction, this catalyst may be recovered according to the reaction represented by Formula 2 below:

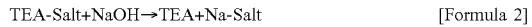

TEA-Salt+NaOH→TEA+Na-Salt    [Formula 2]

By vacuum distillation, a raw material may be discharged, for example, from an upper part of the distillation column (c) and a solution extract including unsaturated aldehyde may be discharged, for example, from a lower part of the distillation column (c).

The raw material may include, for example, an aldehyde compound as a start material, a base catalyst, water, and the like.

The apparatus for generating glycol may further include, for example, a reaction tank in which ion-exchange reaction occurs by adding an inorganic base to a water layer, an aqueous solution, discharged from a lower part of the extractor (b); and a catalyst recovery column for recovering a catalyst for aldol reaction by distilling a basic aqueous solution discharged from the reaction tank.

The apparatus for generating glycol may include, for example, an aldehyde recovery column for recovering an aldehyde compound, as a start material, or the aldehyde compound along with a catalyst from a raw material discharged from the distillation column (c). In this case, the recovered raw material and catalyst may be reused, thereby being very economical.

The apparatus for generating glycol may further include, for example, a water supply pipe for supplying water to a solution extract discharged from the distillation column (c). In this case, generation of high-boiling-point ingredients due to side reaction in a process in which the solution extract is supplied to the hydrogenation reactor may be prevented. In addition, since generation of the high-boiling-point ingredients is suppressed also during hydrogenation, the efficiency of hydrogenation may be greatly increased.

In an embodiment, the water may be added in an amount of 1 to 20 parts by weight, 5 to 15 parts by weight, or 8 to 12 parts by weight based on 100 parts by weight of the solution extract. Within this range, superior reactivity, reaction yield, conversion rate, and glycol selectivity are exhibited.

In another embodiment, the water may be added in an amount of 1 to 20% by weight, 5 to 20% by weight, or 10 to 15% by weight based on 100% by weight of the sum of the solution extract and the water. Within this range, superior reactivity, reaction yield, conversion rate, and glycol selectivity are exhibited.

To the hydrogenation reactor (d), for example, a raw material supply pipe for supplying the solution extract discharged from the distillation column (c); a hydrogen supply pipe for supplying hydrogen; a discharge pipe for discharging a solution product of the hydrogenation; and a recirculation pipe for recirculating a portion of the hydrogenation solution product of the discharge pipe to the hydrogenation reactor may be connected.

The hydrogen supply pipe and the recirculation pipe may be connected to and integrated with, for example, the raw material supply pipe. In this case, dispersion of reactants in a hydrogenation catalyst layer is maximized. Accordingly, the yield of glycol increases and reaction temperature may be easily controlled.

To the raw material supply pipe, for example, a heating device for heating the solution extract immediately before feeding the solution extract into the hydrogenation reactor may be connected. In this case, superior reactivity, reaction yield, conversion rate, and glycol selectivity are exhibited.

At an upper part of the hydrogenation reactor, for example, a distributor may be installed. In this case, dispersion of reactants in a hydrogenation catalyst layer is improved. Accordingly, the yield of glycol increases and reaction temperature may be controlled.

The distributor may be connected to, for example, a raw material supply pipe.

The solution extract may be mixed, for example, with hydrogen gas before the solution extract is supplied to the hydrogenation reactor. In this case, superior hydrogenation yield and glycol conversion rate are exhibited.

The solution extract may be heated, for example, to a hydrogenation temperature immediately before being fed to the hydrogenation reactor. In this case, superior hydrogenation yield and glycol conversion rate are exhibited.

The expression "immediately before being fed to the hydrogenation reactor" may refer to a junction between a point, at which the solution extract and the recirculated hydrogenation solution product meet, and the hydrogenation reactor, or a junction between a point, at which the raw material supply pipe and the recirculation pipe are connected to each other, and the hydrogenation reactor.

The hydrogenation reactor may be, for example, a fixed-bed reactor filled with a copper-based catalyst. In this case, a catalyst and a reaction product are not required to be separated, and reaction temperature and reaction pressure may be lowered compared to conventional cases. Accordingly, stable operation is possible and economic efficiency is superior. In addition, since a catalyst may be easily replaced and the size of the reactor may be reduced, investment costs may be greatly reduced.

The copper-based catalyst may be, for example, a CuO/BaO catalyst. In this case, catalytic performance is superior and the lifespan of the catalyst is long.

The CuO/BaO catalyst may include preferably 60 to 99% by weight of CuO and 1 to 40% by weight of BaO, more preferably 80 to 95% by weight of CuO and 5 to 20% by weight of BaO, most preferably 85 to 90% by weight of CuO and 10 to 15% by weight of BaO. Within this range, the performance of the catalyst is superior and the lifespan of the catalyst is long.

A metal content in the CuO/BaO catalyst may be measured, for example, by ICP analysis.

The copper-based catalyst may include, for example, a silicon oxide support or an aluminum oxide support. In this case, the catalyst exhibits superior performance and properties and the activity of the catalyst may be maintained for a long time.

The copper-based catalyst may be preferably a CuO/BaO/SiO catalyst.

The CuO/BaO/SiO catalyst may be, for example, a catalyst represented by formula (CuO)x(BaO)y(SiO)z, wherein x:y:z=10 to 50:0 to 10:40 to 90, 10 to 50:1 to 10:40 to 89, or 29 to 50:1 to 10:40 to 70, based on % by weight. The sum of x and y is preferably 20 to 50 (% by weight) or 30 to 50 (% by weight) based on 100% by weight of the sum of x, y and z. Within this range, the performance of the catalyst is superior and the lifespan of the catalyst is long.

The temperature of the hydrogenation may b, for example, 50 to 180° C., 130 to 170° C., or 140 to 160° C.

The hydrogenation temperature may be adjusted, for example, by means of a heat exchanger installed at the recirculation pipe and/or a pre-heater installed at the raw material supply pipe. In addition, the hydrogenation temperature may be adjusted by controlling a ratio of the flow rate of supplied raw materials to a recirculated flow rate.

The pressure of the hydrogenation may be, for example, 10 to 250 bar, 20 to 100 bar, or 20 to 50 bar.

An organic solvent and water may be separated and discharged, for example, from an upper part of the divided-wall distillation column, a material having a high boiling point may be separated and discharged, for example, from a lower part of the divided-wall distillation column, and glycol may be discharged, for example, from an intermediate part (side) of the divided-wall distillation column. In this case, energy consumption may be reduced and the number of distillation columns may be reduced, whereby glycol may be prepared in a purity of 99.5% by weight or more with low investment costs.

The organic solvent may be, for example, 2-ethylene hexanol (2-EH), and the material having a high boiling point may be, for example, HPNE and TMPD.

The organic solvent discharged from the upper part of the divided-wall distillation column, for example, is separated and recovered from water by means of a distillation column, and the recovered organic solvent may be recirculated to the extractor via an organic solvent supply pipe.

In addition, the present invention provides a method of preparing glycol by means of the apparatus for generating glycol according to the present disclosure.

The method may further include, for example, a step of adding isobutyraldehyde, an aqueous formaldehyde solution, and an amine compound to an aldol reactor (a) and performing aldol condensation reaction at 70 to 95° C.

The aqueous formaldehyde solution may be, for example, an aqueous solution including 30 to 40% by weight of formaldehyde. In a particular embodiment, the aqueous formaldehyde solution may be formalin.

The amine compound may be, for example, an alkylamine, preferably a trialkylamine, most preferably triethylamine. In this case, aldol condensation reaction is satisfactorily performed and reaction by-products may be easily treated.

The temperature of the aldol condensation reaction is suitably, for example, 70 to 90° C. The residence time of reactants in the reactor is suitably about 1 to 3 hours.

The aldol condensation reaction may be performed, for example, by continuously feeding 1 to 1.3 moles of isobutyraldehyde and 0.03 to 0.1 moles of a catalyst, an amine compound, based on 1 mole of formaldehyde, into an aldol reactor.

In the glycol preparation method, the organic solvent supplied to the extractor (b) may be, for example, a polar organic solvent, preferably alcohol not mixed with water, more preferably 2-ethylene hexanol (2-EH). In this case, extraction efficiency is superior and an organic salt may be efficiently removed. For reference, when an organic salt remains in the aldol product, HPA may be decomposed and by-products may be generated.

In the glycol preparation method, for example, the solution extract fed into the hydrogenation reactor (d) may include 1 to 20% by weight of water based on 100% by weight of the solution extract.

Hereinafter, an apparatus for preparing neopentyl glycol and a method of preparing the same are described in detail with reference to the accompanying drawings.

The drawing is a flowchart schematically illustrating a process of continuously preparing neopentyl glycol according to the present disclosure and an apparatus therefor.

An aqueous formaldehyde solution (FA), isobutyraldehyde (i-BAL) and tetraethylamine (TEA) are respectively, continuously supplied to an aldol reactor via a supply pipe, whereby aldol condensation reaction occurs and thus hydroxypivaldehyde (HPA) is synthesized. Here, the aqueous formaldehyde solution and the isobutyraldehyde may be fed into, for example, the same supply pipe.

An aldol reaction product is continuously supplied to an extractor via a pipe and is mixed with 2-EH separately supplied to extract HPA as an organic layer. The extracted organic layer is discharged from an upper part of the extractor, and supplied to a HPA distillation column (HPA column) via a pipe.

A water layer discharged from a lower part of the extractor is treated with NaOH (not shown) and then transferred to a TEA column to separate and recover TEA. The recovered TEA is re-supplied to the aldol reactor via a pipe.

A suitable temperature of the extractor is 40 to 70° C. To effectively remove organic acid, organic acid salt of triethylamine, and the like, as water-soluble side reactants, during an extraction process, water may be additionally fed into the extractor.

Excess low-boiling-point isobutyraldehyde, triethylamine, water, and the like of aldol reaction products are discharged from an upper part of the HPA column. The discharged isobutyraldehyde, triethylamine, and the like are recovered and re-supplied to the aldol reactor.

An HPA solution, which includes HPA, as a bottom region material of the HPA column, and 2-EH dissolved in the HPA, is continuously supplied into a hydrogenation reactor fixed with a copper-based catalyst via a pipe, and hydrogenation is carried out by adding hydrogen separately supplied. The hydrogenation may be carried out at 120 to 180° C. under a pressure of 10 to 100 bar.

Crude NPG produced by means of the hydrogenation reactor is supplied into the divided-wall distillation column (DWC column) via a pipe, and is isolated and obtained as neopentyl glycol having a purity of 99.5% by weight or more. 2-EH and water, which are separated and discharged from the top of the divided-wall distillation column, are distilled by means of a 2-EH distillation column, thereby recovering 2-EH. The recovered 2-EH is recirculated to the extractor via a pipe.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

EXAMPLE

Example 1

HPA Preparation 6.7 kg/hr of i-BAL, 7.0 kg/hr of aqueous 37% HCHO solution, and 0.8 kg/hr of TEA were continuously supplied into a 20 L jacketed reactor (3 series CSTR aldol reactor). Reaction was carried out while maintaining this reactor under conditions of 90° C. and a pressure of 2 bar. As a result, an aldol reaction product having a composition summarized in Table 1 below was obtained at a rate of 14.5 kg/hr.

Continuous operation was carried out while supplying the aldol reaction product to a raw material supply stage located at an upper part of a 30-stage multi-stage extractor at a rate of 6.2 kg/hr, supplying 2-EH to an extractant supply stage located at a lower part of the extractor at a rate of 1.7 kg/hr, and maintaining the temperature of the extractor at 66° C. Here, TEA salt ingredients and water were simultaneously separated in a lowest stage of the extractor, and an organic layer containing HPA was continuously separated in a highest stage of the extractor. The composition of the organic layer extracted and then separated is summarized in Table 1 below.

The organic layer, which has been separated by means of the extractor, was vacuum-distilled by means of a distillation column having 50 mm 15 stages, the temperature of a lower part of which was 90° C. As a result, i-BAL and TEA, as effective ingredients, were recovered in an upper part of the distillation column, and a 2-EH solution containing an HPA ingredient, as a raw material of the hydrogenation, was separated in a lower part of the distillation column. The composition of the separated HPA-containing 2-EH solution is summarized in Table 1 below.

TABLE 1

| Classification | Aldol reaction product | Organic layer after extraction | Unit: % by weight Organic layer after HPA column purification |
|---|---|---|---|
| iBAL | 2.5 | 1.1 | 0.1 |
| FA | 0.2 | 0.3 | 0.3 |
| MeOH | 2.2 | 1.9 | 0.0 |
| TEA | 3.1 | 2.3 | 0.4 |
| H$_2$O | 25 | 12.6 | 3.0 |
| HPA | 48 | 41.1 | 53.1 |
| NPG | 1.2 | 1.3 | 1.7 |
| 2-EH | 0 | 22.5 | 26.7 |

TABLE 1-continued

| Classification | Aldol reaction product | Organic layer after extraction | Unit: % by weight Organic layer after HPA column purification |
|---|---|---|---|
| NPG ester | 8.4 | 5.3 | 7.7 |
| Others | 9.4 | 11.7 | 7.0 |

Example 2

Preparation and Purification of Crude NPG 10 parts by weight of distilled water were added to 100 parts by weight of an HPA-containing 2-EH solution prepared according to Example 1, thereby preparing a raw material suitable for hydrogenation. The composition of the prepared raw material is summarized in Table 2 below.

The raw material for hydrogenation was constantly supplied to a fixed-bed adiabatic reactor filled with a copper-based catalyst at a flow rate of 0.2 kg/hr. Here, a silica-supported copper-based catalyst, i.e., CuO/BaO/SiO (Cu:Ba:Si=40:5:55 (weight ratio)), was used as a copper-based catalyst. The temperature and pressure of a reactor inlet were respectively 140° C. and 40 bar. Operation was continuously performed for 24 hr. The composition of an obtained hydrogenation product is summarized in Table 2 below.

The hydrogenation product was vacuum-distilled by means of a divided-wall column (DWC). Here, the temperatures of a raw material supply stage and upper and lower parts of the DWC were respectively 155° C., 129° C., and 177° C. A high-purity NPG product was continuously isolated and obtained from a side of the DWC. The composition of the obtained NPG product is summarized in Table 2 below.

TABLE 2

| Classification | Hydrogenation reaction raw material | Hydrogenation reaction product | Unit: % by weight Composition of NPG product |
|---|---|---|---|
| iBAL | 0.1 | 0.0 | 0.0 |
| FA | 0.3 | 0.0 | 0.0 |
| MeOH | 0.0 | 0.4 | 0.0 |
| TEA | 0.4 | 0.3 | 0.0 |
| H$_2$O | 13.0 | 13.8 | 0.2 |
| HPA | 48.8 | 0.1 | 0.0 |
| NPG | 1.5 | 57.1 | 99.6 |
| 2-EH | 24.0 | 24.9 | 0.0 |
| NPG ester | 6.9 | 1.0 | 0.0 |
| Others | 5.0 | 2.4 | 0.2 |

As shown in Table 2, it can be confirmed that, by using the method of the present disclosure, a high-purity NPG product having a purity of 99.6% by weight may be continuously prepared without application of an excessive reaction condition or a complex purification process.

Comparative Example 1

NPG was prepared and purified and an NPG product was continuously isolated and obtained in the same manner as in Example 2, except that a catalyst layer composed a nickel-based catalyst (Ni:NiO:Cr$_2$O$_3$:Kieselguhr=30:26:15:29 (weight ratio)) was used instead a catalyst layer composed of the silica-supported copper-based catalyst in a hydrogenation reactor. The compositions of an obtained hydrogenation product and NPG product are summarized in Table 3 below.

TABLE 3

| Classification | Hydrogenation reaction raw material | Hydrogenation reaction product | Unit: % by weight Composition of NPG product |
|---|---|---|---|
| iBAL | 0.1 | 0.1 | 0.0 |
| FA | 0.3 | 0.0 | 0.0 |
| MeOH | 0 | 0.4 | 0.0 |
| TEA | 0.4 | 0.3 | 0.0 |
| $H_2O$ | 13 | 13.9 | 0.2 |
| HPA | 48.8 | 0.4 | 0.0 |
| NPG | 1.5 | 56.2 | 99.3 |
| 2-EH | 24 | 24.9 | 0.1 |
| NPG ester | 6.9 | 1.1 | 0.0 |
| Others | 5 | 2.7 | 0.4 |

As shown in Table 3, it can be confirmed that, when the apparatus for preparing glycol according to the present disclosure and the method of preparing the same are used, but a different hydrogenation catalyst is used, a proportion of unreacted remainders, i-BAL and HPA ingredients, in a hydrogenation product increases. In addition, it can be confirmed that, when an NPG product is isolated by vacuum distillation using the hydrogenation product, the purity of the NPG product is decreased.

The invention claimed is:

1. An apparatus for generating glycol, comprising:
(a) an aldol reactor;
(b) an extractor for extracting an aldol product, unsaturated aldehyde, using an organic solvent that is not mixed with water;
(c) a distillation column for removing a raw material from a solution extract that is discharged from the extractor;
(d) a hydrogenation reactor for hydrogenating a solution extract that is discharged from the distillation column; and
(e) a divided-wall distillation column for isolating glycol from a hydrogenated solution product that is discharged from the hydrogenation reactor,
wherein the hydrogenation reactor is a fixed-bed catalytic reactor that is filled with a copper-based catalyst, and
wherein the apparatus comprises a reaction tank in which ion-exchange reaction occurs by adding an inorganic base to a water layer, an aqueous solution, discharged from the extractor (b); and a catalyst recovery column for recovering a catalyst for aldol reaction by distilling a basic aqueous solution discharged from the reaction tank.

2. The apparatus according to claim 1, wherein the aldol reactor (a) is a jacketed reactor.

3. The apparatus according to claim 1, wherein the aldol product of the extractor (b) is hydroxypivaldehyde, and the glycol of the divided-wall distillation column (e) is neopentyl glycol.

4. The apparatus according to claim 1, wherein the extractor comprises an aldol product inlet, an extractant inlet, an organic layer outlet, and a water layer outlet.

5. The apparatus according to claim 1, wherein, by vacuum distillation, a raw material is discharged from an upper part of the distillation column (c) and a solution extract comprising unsaturated aldehyde is discharged from a lower part of the distillation column (c).

6. The apparatus according to claim 1, further comprising a water supply pipe for supplying water to a solution extract discharged from the distillation column (c).

7. The apparatus according to claim 1, further comprising an aldehyde recovery column for recovering a start material, an aldehyde compound, from a raw material discharged from the distillation column (c).

8. The apparatus according to claim 1, wherein the copper-based catalyst is a CuO/BaO catalyst.

9. The apparatus according to claim 8, wherein the copper-based catalyst is a CuO/BaO/SiO catalyst.

10. The apparatus according to claim 1, wherein an organic solvent and water are separated and discharged from an upper part of the divided-wall distillation column, a material having a high boiling point is separated and discharged from a lower part of the divided-wall distillation column, and glycol is discharged from an intermediate part of the divided-wall distillation column.

11. A method of preparing glycol by means of the apparatus according to claim 1.

12. The method according to claim 11, further comprising a step of adding isobutyraldehyde, an aqueous formaldehyde solution, and an amine compound to an aldol reactor (a) and performing aldol condensation reaction at 70 to 95 ° C.

13. The method according to claim 11, wherein an organic solvent supplied to an extractor (b) is a polar organic solvent.

14. The method according to claim 11, wherein a solution extract fed into a hydrogenation reactor (d) comprises 1 to 20% by weight of water based on 100% by weight of the solution extract.

* * * * *